US00PP13610P2

(12) United States Plant Patent
Trees

(10) Patent No.: US PP13,610 P2
(45) Date of Patent: Mar. 4, 2003

(54) GERANIUM PLANT NAMED 'BALSHOFRON'

(75) Inventor: Scott C. Trees, Shell Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/115,061

(22) Filed: Apr. 1, 2002

(51) Int. Cl.[7] ..... A01H 5/00
(52) U.S. Cl. ..... Plt./325
(58) Field of Search ..... Plt./325, 320

*Primary Examiner*—Kent L. Bell
(74) *Attorney, Agent, or Firm*—C. A. Whealy

(57) ABSTRACT

A new and distinct cultivar of Geranium plant named 'Balshofron', characterized by its upright and mounded growth habit; freely basal branching habit; dark green-colored leaves; and red and white bi-colored semi-double flowers.

1 Drawing Sheet

BOTANICAL CLASSIFICATION/CULTIVAR DESIGNATION

*Pelargonium×hortorum* cultivar 'Balshofron'.

BACKGROUND OF THE INVENTION

The present invention relates to a new and distinct cultivar of Geranium plant, botanically known as *Pelargonium×hortorum*, and hereinafter referred to by the name 'Balshofron'.

The new Geranium is a product of a planned breeding program conducted by the inventor in Arroyo Grande, Calif. The objective of the breeding program is to develop new compact Zonal Geranium cultivars that flower uniformly and have attractive flower and foliage colors.

The new Geranium originated from a cross-pollination made by the inventor in June, 2000 of a proprietary *Pelargonium×hortorum* selection identified as code number 8693-4, not patented, as the female, or seed, parent with a proprietary *Pelargonium×hortorum* selection identified as code number 8695-25, not patented, as the male, or pollen, parent. The cultivar 'Balshofron' was discovered and selected by the inventor as a flowering plant within the progeny from this cross-pollination in a controlled environment in Arroyo Grande, Calif.

Asexual reproduction of the new cultivar by terminal cuttings taken at Arroyo Grande, Calif., since June, 2000 has shown that the unique features of this new Geranium are stable and reproduced true to type in successive generations of asexual reproduction.

SUMMARY OF THE INVENTION

The following traits have been repeatedly observed and are determined to be the unique characteristics of 'Balshofron'. These characteristics in combination distinguish 'Balshofron' as a new and distinct Geranium cultivar:

1. Upright and mounded growth habit.
2. Freely basal branching habit.
3. Dark green-colored leaves.
4. Red and white bi-colored semi-double flowers.

Plants of the new Geranium differ primarily from plants of the female parent selection in leaf coloration. Plants of the new Geranium differ primarily from plants of the male parent selection in flower form.

The new Geranium can be compared to the cultivar, 'BFP-1705', disclosed in U.S. Plant Pat. No. 11,396. However, in side-by-side comparisons conducted in West Chicago, Ill., plants of the new Geranium differed from plants of the cultivar 'BFP-1705' in the following characteristics:

1. Plants of the new Geranium were more compact with shorter lateral branches and internodes than plants of the cultivar 'BFP-1705'.
2. Leaves of plants of the new Geranium did not have a distinct zonation pattern whereas leaves of plants of the cultivar 'BFP-1705' had a distinct zonation pattern.
3. Plants of the new Geranium had slightly smaller flowers than plants of the cultivar 'BFP-1705'.
4. Plants of the new Geranium and the cultivar 'BFP-1705' differed in flower coloration.
5. Plants of the new Geranium had shorter peduncles than plants of the cultivar 'BFP-1705'.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical flowering plant of 'Balshofron'. Flower and foliage colors in the photograph differ slightly from the color values cited in the detailed botanical description which accurately describe the colors of the new Geranium.

DETAILED BOTANICAL DESCRIPTION

The cultivar 'Balshofron' has not been observed under all possible environmental conditions. The phenotype may vary somewhat with variations in environment such as temperature and light intensity, without, however, any variance in genotype. The aforementioned photograph and following observations and measurements describe plants grown in West Chicago, Ill., under commercial practice in a polycarbonate-covered greenhouse with day temperatures about 20 to 22° C., night temperatures about 18 to 20° C. and light levels about 2,500 to 3,000 foot-candles. Plants used for the photograph and description were about 11 to 13 weeks from planting rooted cuttings. In the following description, color references are made to The Royal Horticultural Society Colour Chart, 1995 Edition, exept where general terms of ordinary dictionary significance are used.

Botanical classification:

*Pelargonium×hortorum* cultivar 'Balshofron'.

Parentage:

*Female parent.*—Proprietary *Pelargonium×hortorum* selection identified as code number 8693-4, not patented.

*Male parent.*—Proprietary *Pelargonium×hortorum* selection identified as code number 8695-25, not patented.

Propagation:

*Type cutting.*—Terminal cuttings.

*Time to initiate roots.*—About 7 days at 18° C.

*TIme to develop roots.*—About 21 days at 18° C.

*Root description.*—Fibrous, freely branching.

Plant description:

*General appearance.*—Upright and mounded growth habit. Appropriate for 10-cm and larger containers.

*Growth and branching habit.*—Vigorous and freely basal branching with about three lateral branches at the base. Pinching, that is, removal of terminal apices, is typically not required.

*Plant height* (*to top of foliage*).—About 13.8 cm.

*Plant width.*—About 20.8 cm.

*Lateral branches.*—Length: About 9 cm. Internode length: About 1.3 cm. Texture: Pubescent. Color: 146C overlain with 175A.

*Foliage description.*—Arrangement: Opposite, simple. Quantity of leaves per lateral branch: About 13. Length: About 4.7 cm. Width: About 7.8 cm. Shape: Reniform. Apex: Rounded. Base: Cordate. Margin: Crenate. Venation: Palmate. Texture, upper and lower surfaces: Velvety; pubescent. Color: Young and fully expanded foliage, upper surface: 147A; no distinct zonation pattern. Young and fully expanded foliage, lower surface: 146A. Venation, upper surface: 144B. Venation, lower surface: 146D. Petiole: Length: About 4.5 cm. Diameter: About 3 mm. Texture, upper and lower surfaces: Pubescent. Color, upper and lower surfaces: 146A.

Flower description:

*Flower arrangement and type.*—Single flowers arranged in hemispherical umbels arising from apical leaf axils. Umbels displayed above the foliage. At full flowering, ususally about five open umbels and about three developing umbels per plant. Flowers semi-double and rounded in shape. Umbels persistent. Flowers not fragrant.

*Flowering season.*—Year-round under greenhouse conditions. In the garden, flowering is continuous from spring until fall. Plants start flowering about eleven weeks after planting.

*Flowering longevity.*—Flowers last about ten days on the plant.

*Umbels.*—Diameter: About 7.4 cm. Height: About 4.6 cm. Number of flowers per umbel: About 15. Flower diameter: About 3.6 cm. Flower depth (height): About 1 cm.

*Flower buds.*—Length: About 1.4 cm. Diameter: About 6 mm. Shape: Ovoid. Color: 51A.

*Petals/petaloids.*—Quantity: About seven petals and about two or three petaloids per flower. Petaloids variable in size and shape. Arrangement: Imbricate. Petal length: Upper petals: About 2.2 cm. Lower petals: About 1.9 cm. Petal width: Upper petals: About 1.6 cm. Lower petals: About 1.7 cm. Petal shape: Obovate. Petal/Petaloid apex: Rounded, obtuse. Petal/petaloid base: Attenuate. Petal/petaloid margin: Entire. Petal/petaloid texture, upper and lower surfaces: Smooth. Petal/petaloid aspect: Slightly cupped. Petal/petaloid color: When opening and fully opened, upper surface: Towards base, 155D; gradually fading to lighter than 44D towards apex; at margin, 55D; venation, 51A. When opening and fully opened, lower surface: 55D; venation, lighter than 44D.

*Sepals.*—Quantity: Five per flower; not imbricate on open flowers. Length: About 9 mm. Width: About 3 mm. Shape: Ensiform to lanceolate. Apex: Acuminate. Margin: Entire. Texture, upper surface: Glabrous. Texture, lower surface: Pilose. Color, upper surface: 146A. Color, lower surface: 146B.

*Peduncle* (*umbel stem*).—Length: About 7.5 cm. Angle: Erect. Strength: Strong. Texture: Pubescent. Color: 146C overlain with 175A.

*Pedicel* (*individual flower stem*).—Length: About 2.5 cm. Angle: Erect. Strength: Strong. Texture: Pubescent. Color: 146C overlain with 175A.

*Reproductive organs.*—Androecium: Anther quantity: Five per flower. Anther length: About 2 mm. Anther color: 51B. Pollen amount: Moderate. Pollen color: 168A. Gynoecium: Pistil quantity: One per flower. Pistil length: About 8 mm. Stigma shape: Five-parted, star-shaped. Stigma color: 42A. Style length: About 3 mm. Style color: 31D.

*Seed/fruit.*—None observed.

Disease/pest resistance: Resistance to pathogens and pests common to Pelargonium has not been observed.

It is claimed:

1. A new and distinct cultivar of Geranium plant named 'Balshofron', as herein illustrated and described.

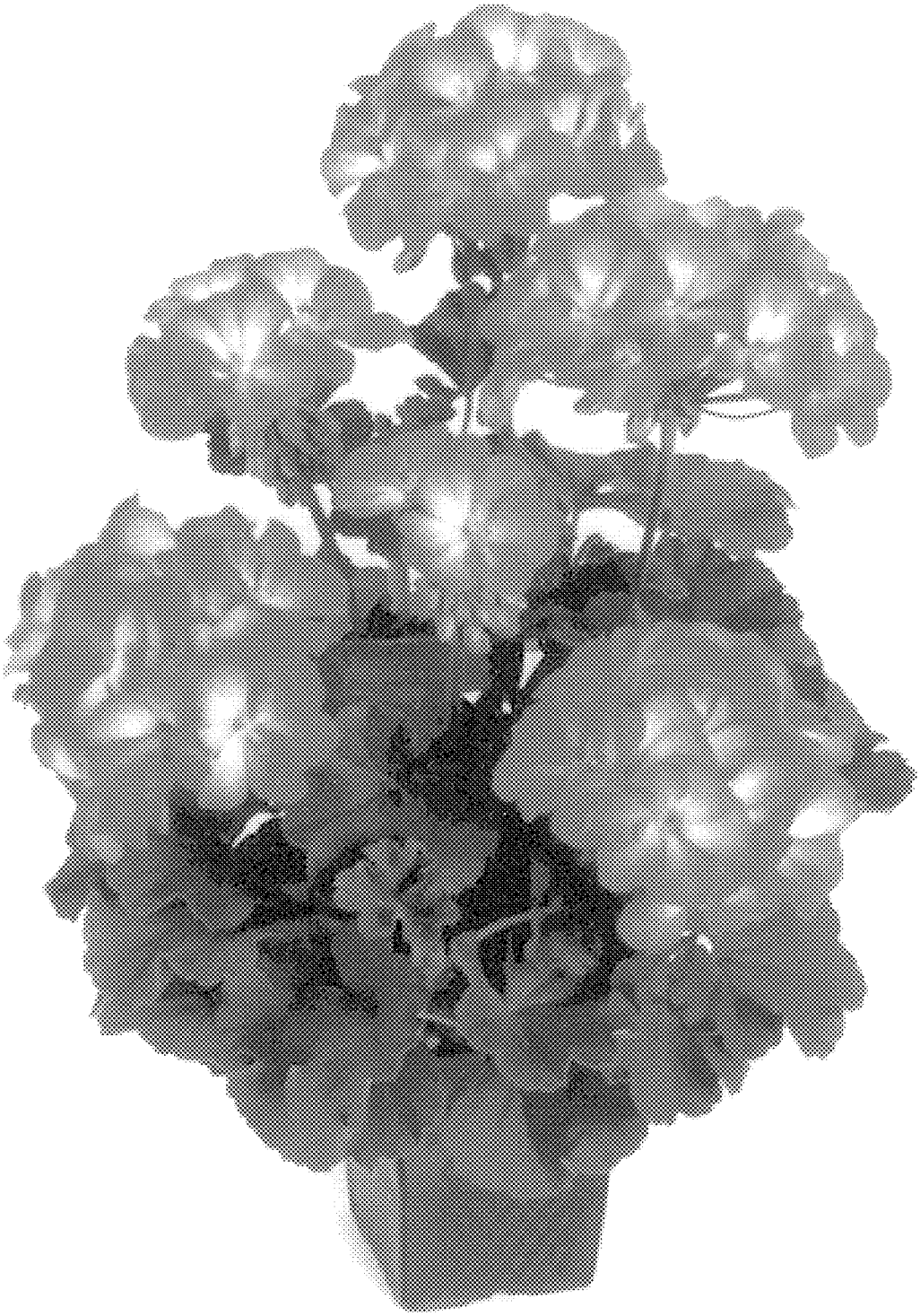

* * * * *